(12) United States Patent
DeVasConCellos

(10) Patent No.: US 10,441,317 B2
(45) Date of Patent: Oct. 15, 2019

(54) BONE FIXATION SYSTEM AND METHOD USING A CLAMPING INSTRUMENT TO GUIDE FASTENER PLACEMENT

(71) Applicant: SIGN Fracture Care International, Richland, WA (US)

(72) Inventor: Paul DeVasConCellos, Richland, WA (US)

(73) Assignee: SIGN Fracture Care International, Richland, WA (US)

(*) Notice: Subject to any disclaimer, the term of this patent is extended or adjusted under 35 U.S.C. 154(b) by 259 days.

(21) Appl. No.: 15/658,198

(22) Filed: Jul. 24, 2017

(65) Prior Publication Data
US 2018/0110542 A1 Apr. 26, 2018

Related U.S. Application Data

(60) Provisional application No. 62/413,212, filed on Oct. 26, 2016.

(51) Int. Cl.
A61B 17/64 (2006.01)
A61B 17/62 (2006.01)
(Continued)

(52) U.S. Cl.
CPC ...... *A61B 17/6441* (2013.01); *A61B 17/1615* (2013.01); *A61B 17/62* (2013.01); *A61B 17/645* (2013.01); *A61B 17/6425* (2013.01); *A61B 17/683* (2013.01); *A61B 17/844* (2013.01); *A61B 17/86* (2013.01); *A61B 17/8866* (2013.01); *A61B 17/17* (2013.01); *A61B 2017/088* (2013.01)

(58) Field of Classification Search
CPC .......... A61B 17/6441; A61B 2017/088; A61B 17/844; A61B 17/17
See application file for complete search history.

(56) References Cited

U.S. PATENT DOCUMENTS 2,434,431 A * 1/1948 Pincock ................. A61B 17/17
606/104
2,485,531 A 10/1949 Dzus et al.
(Continued)

OTHER PUBLICATIONS

Acumed LLC, "Wrist Plating System" Surgical Technique Brochure, (c) 2014 pp. 1-36.
(Continued)

*Primary Examiner* — Christian A Sevilla
(74) *Attorney, Agent, or Firm* — Kolisch Hartwell, P.C.

(57) ABSTRACT

System and method for fixing bone. An exemplary system may comprise a clamping instrument, a first fastener, and a second fastener. The clamping instrument may include a first tube and a second tube. The tubes may have an adjustable separation from one another while remaining coaxially aligned with one another on an axis, and may be configured to apply pressure to opposite sides of a bone to compress the bone. The first fastener may be configured to pass through the first tube on the axis. The second fastener may be configured to attach to the first fastener and to pass through the second tube on the axis. In some embodiments, the system also may comprise an insertion tool configured to carry the second fastener into the second tube and prevent the second fastener from turning.

18 Claims, 12 Drawing Sheets

(51) Int. Cl.
  *A61B 17/16* (2006.01)
  *A61B 17/17* (2006.01)
  *A61B 17/86* (2006.01)
  *A61B 17/84* (2006.01)
  *A61B 17/68* (2006.01)
  *A61B 17/88* (2006.01)
  *A61B 17/08* (2006.01)

(56) References Cited

U.S. PATENT DOCUMENTS

| | | | |
|---|---|---|---|
| 2,511,051 A | 6/1950 | Dzus | |
| 2,908,309 A | 10/1959 | Brill | |
| 4,399,813 A * | 8/1983 | Barber | A61B 17/1615 606/100 |
| 4,456,005 A | 6/1984 | Lichty | |
| 4,790,304 A | 12/1988 | Rosenberg | |
| 5,009,134 A | 4/1991 | Sorensen et al. | |
| 5,098,433 A | 3/1992 | Freedland | |
| 5,108,399 A | 4/1992 | Eitenmuller et al. | |
| 5,269,784 A | 12/1993 | Mast | |
| 5,899,906 A | 5/1999 | Schenk | |
| 6,010,505 A | 1/2000 | Asche et al. | |
| 6,146,384 A | 11/2000 | Lee et al. | |
| 6,302,887 B1 | 10/2001 | Spranza et al. | |
| 6,605,090 B1 | 8/2003 | Trieu et al. | |
| 6,918,912 B2 | 7/2005 | Seemann | |
| 7,410,496 B2 | 8/2008 | Derouet | |
| 7,704,257 B2 | 4/2010 | Mürner | |
| 8,002,812 B2 | 8/2011 | Falahee et al. | |
| 8,388,667 B2 | 3/2013 | Reiley et al. | |
| 8,998,969 B2 | 4/2015 | Deffenbaugh et al. | |
| 9,247,963 B2 | 2/2016 | Kollmer | |
| 10,299,830 B2 * | 5/2019 | Cresina | A61B 17/645 |
| 2003/0120273 A1 * | 6/2003 | Cole | A61B 17/66 606/57 |
| 2007/0123857 A1 * | 5/2007 | Deffenbaugh | A61B 17/025 606/54 |
| 2008/0234664 A1 * | 9/2008 | May | A61B 17/1615 606/1 |
| 2012/0116410 A1 * | 5/2012 | Kortenbach | A61B 17/17 606/96 |
| 2013/0158556 A1 * | 6/2013 | Jones | A61B 17/157 606/87 |
| 2016/0367291 A1 * | 12/2016 | Erickson | A61B 17/645 |
| 2018/0110542 A1 * | 4/2018 | DeVasConCellos | A61B 17/683 |
| 2018/0132897 A1 * | 5/2018 | Shiner | A61B 17/6466 |

OTHER PUBLICATIONS

Cuadrado, A. et al., "Suitability of DCPs with Screw Locking Elements to allow sufficient interfragmentary motion to promote secondary bone healing of osteoporotic fractures", Medical Engineering & Physics, vol. 35, (2013) pp. 852-859.

Depuy Synthes GMBH, "Pelvic C-Clamp" Surgical Technique Brochure, (c) 2016, pp. 1-20.

Garcés, Gerardo L. et al., "Use of screw locking elements improves radiological and biomechanical results of femoral osteotomies", BMC Musculoskeletal Disorders, vol. 15, No. 387, pp. 1-8.

Stryker Trauma GMBH, "T2 R1.5 Femoral Nailing SYstem" Operative Technique Brochure, (c) 2010, pp. 1-60.

Synthes, Inc., "Collinear Reduction Clamp" Brochure, (c) 2007, pp. 1-8.

Yánez, A. et al., "Biomechanical evaluation of a new system to improve screw fixation in osteoporotic bones", Medical Engineering & Physics, vol. 32, (2010) pp. 532-541.

Yánez, A. et al., "A New System to Improve Screw Fixation to Bones", Journal of Medical Devices, vol. 5, Dec. 2011, 5 pages.

Yánez, A. et al., "Screw locking elements: A means to modify the flexibility of osteoporotic fracture fixation with DCPs without compromising system strength or stability", Medical Engineering & Physics, vol. 34, (2012) pp. 717-724.

Yánez, A. et al., "Experimental analysis of the minimally invasive plate osteosynthesis technique applied with non-locking screws and screw locking elements", Medical Engineering & Physics, vol. 36, (2014) pp. 1543-1548.

* cited by examiner

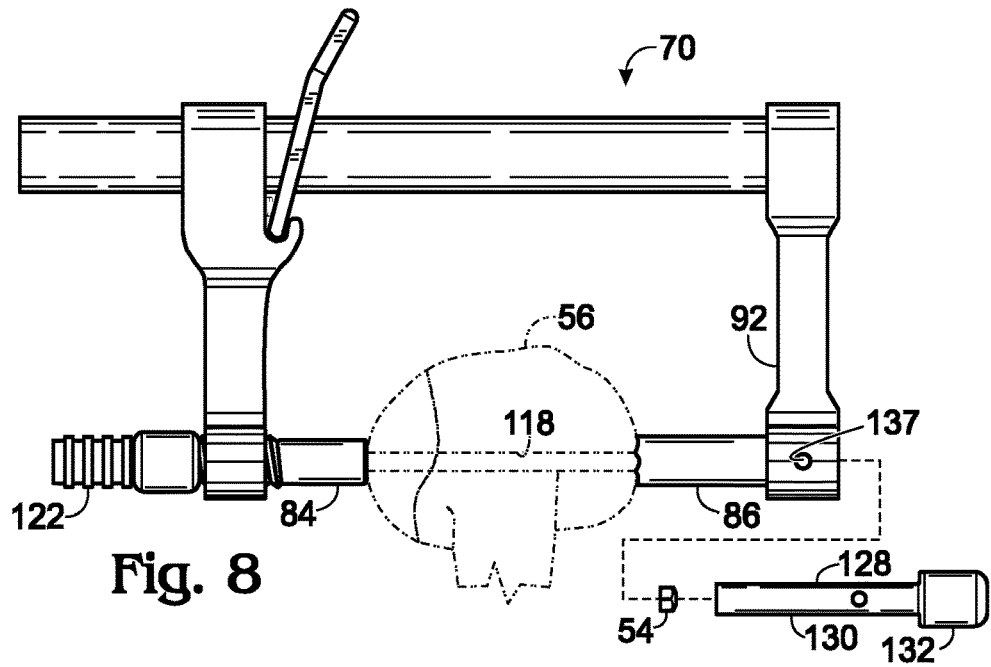
Fig. 8
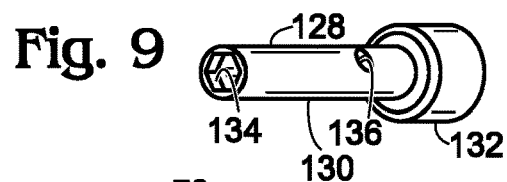
Fig. 9
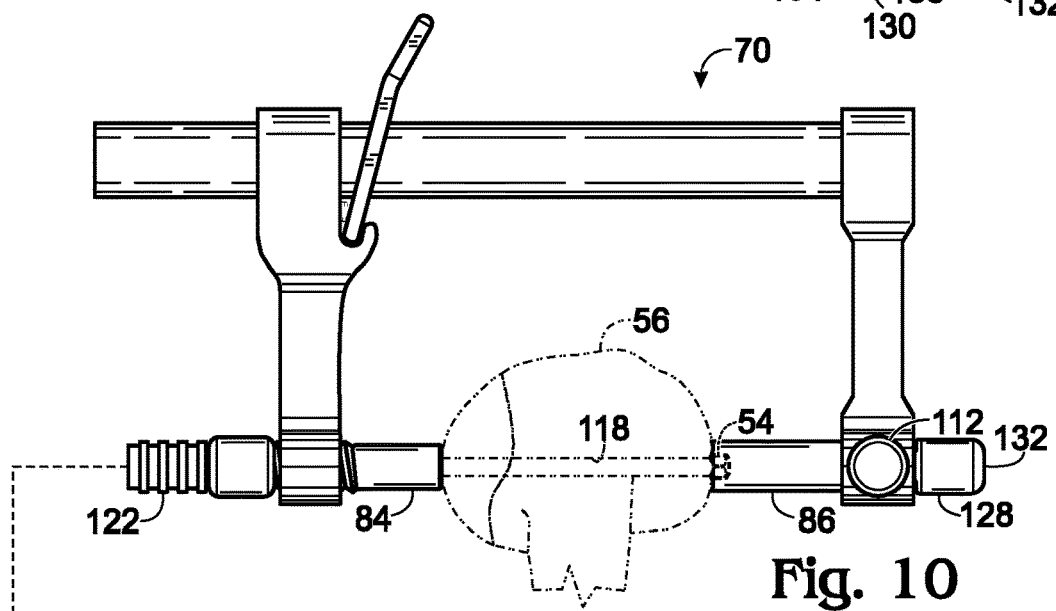
Fig. 10
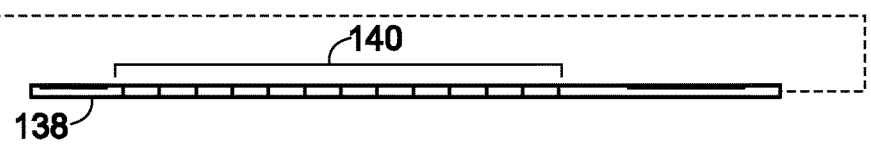

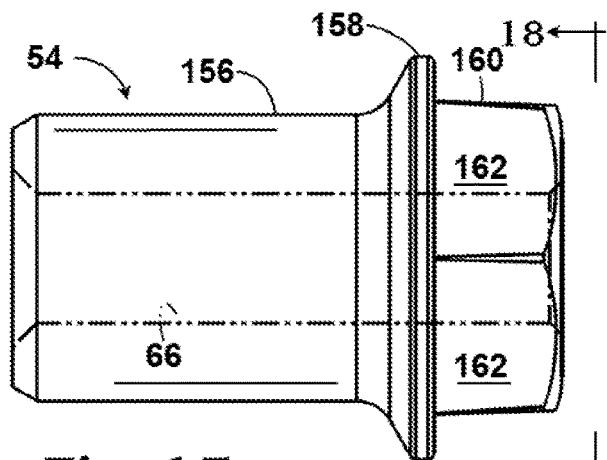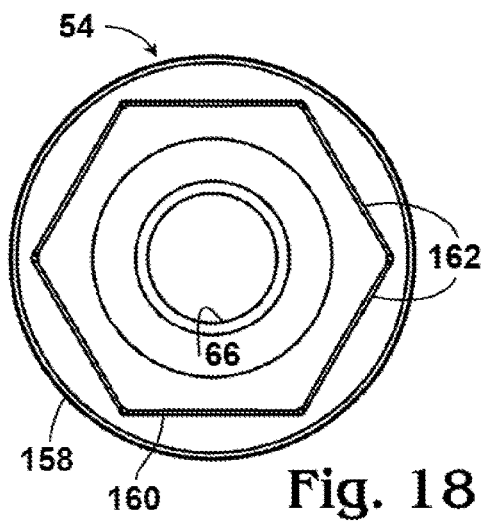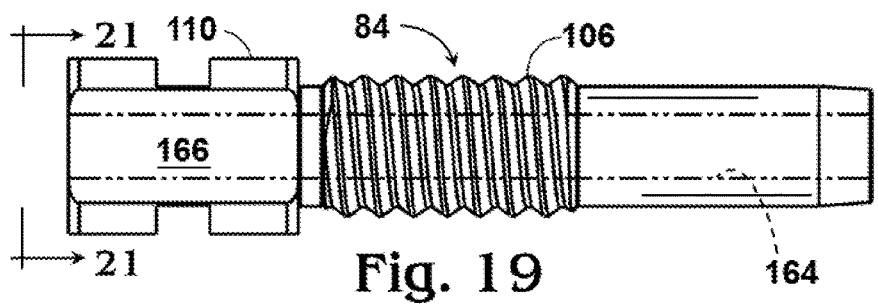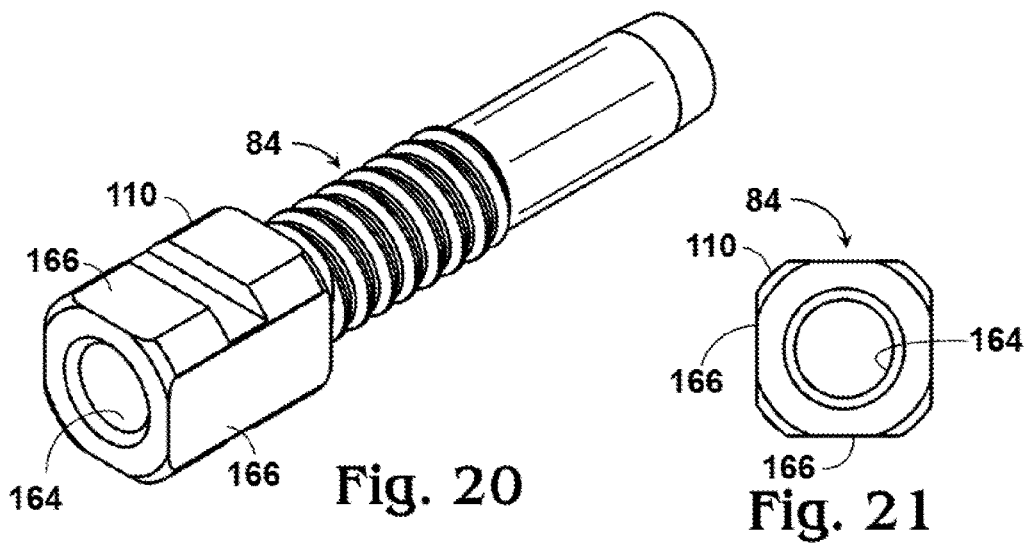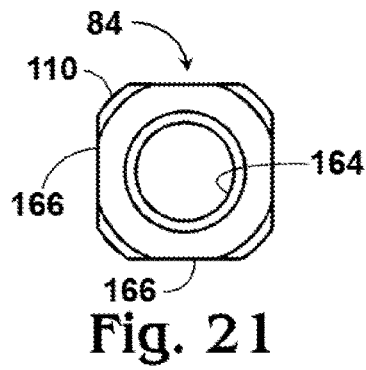

BONE FIXATION SYSTEM AND METHOD USING A CLAMPING INSTRUMENT TO GUIDE FASTENER PLACEMENT

CROSS-REFERENCE TO PRIORITY APPLICATION

This application is based upon and claims the benefit under 35 U.S.C. § 119(e) of U.S. Provisional Patent Application Ser. No. 62/413,212, filed Oct. 26, 2016, which is incorporated herein by reference in its entirety for all purposes.

INTRODUCTION

There are many types and causes of bone fractures, but the goal of treatment is the same: to restore the bone to a functional anatomic shape. This often involves surgical intervention in which fragments of the bone are manipulated and then fixed and supported with the addition of hardware. Hardware options vary greatly, as do the specific needs for successful fixation and repair of different bones and/or different types of fractures. The hardware may be applied inside bone, on bone, outside soft tissue, or a combination of all three.

In some cases, compression across the fracture line can be beneficial. Historically, this has been accomplished with instruments such as clamps, and/or implants such as lag screws. This compression, which acts to move fragments of bone toward each other, can add stability to a fracture by pressing the fragments against one another to generate friction along the fracture line. The friction resists movement that may be caused by patient weight-bearing or motion. Also, the compression can promote healing of the bone. Thus, compression of bone fragments can play an important role in fracture fixation.

Successful fixation with a lag screw generally depends on the presence of high quality bone around the fracture. Otherwise, the threads of the lag screw may strip the bone, thereby losing compression. For fixation of low quality bone, it may be beneficial to implant a device able to apply compressive load to the exterior bone surface, while removing a minimal amount of bone material. However, better instruments for implanting such a device are needed.

SUMMARY

The present disclosure provides a system and method for fixing bone. An exemplary system may comprise a clamping instrument, a first fastener, and a second fastener. The clamping instrument may include a first tube and a second tube. The tubes may have an adjustable separation from one another while remaining coaxially aligned with one another on an axis, and may be configured to apply pressure to opposite sides of a bone to compress the bone. The first fastener may be configured to pass through the first tube on the axis. The second fastener may be configured to attach to the first fastener and to pass through the second tube on the axis. In some embodiments, the system also may comprise an insertion tool configured to carry the second fastener into the second tube and prevent the second fastener from turning.

BRIEF DESCRIPTION OF THE DRAWINGS

FIG. 8 is an elevational view of the clamping instrument, guide member, and bone of FIG. 7, taken in the presence of a female fastener and an insertion tool therefor, after a boring tool has created a hole through the bone, with the female fastener and its insertion tool exploded from each other and their operative sites in the clamping instrument, in accordance with aspects of the present disclosure.

FIG. 9 is a view of the insertion tool of FIG. 8 oriented to reveal a recess that receives at least a portion of the female fastener and restricts movement thereof, in accordance with aspects of the present disclosure.

FIG. 10 is an elevational view of the clamping instrument, guide member, female fastener, insertion tool, and bone of FIG. 8, taken after the insertion tool has been mated with the clamping instrument to operatively position the female fastener at a far end of the hole, and also taken in the presence of a depth gauge to measure the depth/length of the hole, with the depth gauge exploded from its operative position in the clamping instrument and hole, in accordance with aspects of the present disclosure.

FIG. 17 is a side view of a female fastener for a fastener assembly of the bone fixation system of FIG. 16.

FIG. 18 is an end view of the female fastener of FIG. 17, taken generally along line 18-18 of FIG. 17.

FIG. 19 is a side view of an externally threaded tube of a clamping instrument of the bone fixation system of FIG. 16.

FIG. 20 is an isometric view of the tube of FIG. 19.

FIG. 21 is an outer end view of the tube of FIG. 19, taken generally along line 21-21 of FIG. 19.

DETAILED DESCRIPTION

Figure 1:
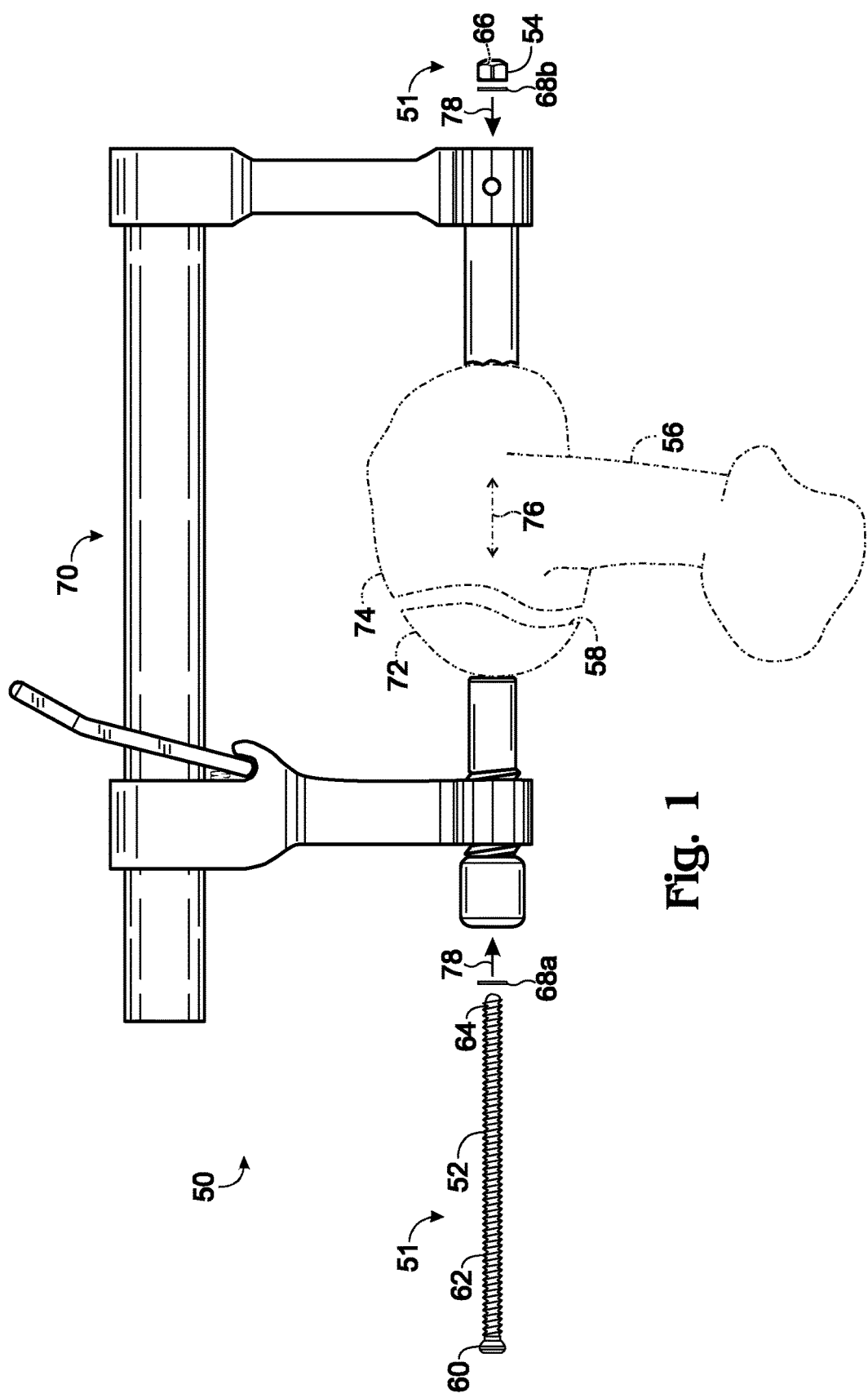
FIG. 1 is an elevational view of selected aspects of an exemplary bone fixation system including a pair of fasteners that attach to one another to form a fastener assembly, and a clamping instrument to engage a bone (shown in phantom outline) and guide installation of the fasteners, in accordance with aspects of the present disclosure.

The present disclosure provides a system and method for fixing bone. An exemplary system may comprise a clamping instrument, a first fastener, and a second fastener. The clamping instrument may include a first tube and a second tube. The tubes may have an adjustable separation from one another while remaining coaxially aligned with one another on an axis, and may be configured to apply pressure to opposite sides of a bone to compress the bone. The first fastener may be configured to pass through the first tube on the axis. The second fastener may be configured to attach to the first fastener and to pass through the second tube on the axis. In some embodiments, the system also may comprise an insertion tool configured to carry the second fastener into the second tube and prevent the second fastener from turning.

A method of fixing bone is provided. In the method, a bone may be compressed with a clamping instrument. The clamping instrument may have a first tube and a second tube that apply pressure to opposite sides of the bone and are coaxially aligned with one another on an axis. A hole may be created through the bone on the axis. A leading end of a first fastener may be passed through the first tube and into the hole. A second fastener may be inserted into the second tube along the axis. The first and second fasteners may be attached to one another by threaded engagement. The steps of creating, passing, inserting, and attaching may be performed while the first and second tubes remain engaged with the bone.

With the clamping instrument in place, an accessory may be placed into the clamping instrument to act as a drill guide for the appropriate size boring tool to form a hole through the bone, and across the fracture line(s). At this stage, a female fastener may not yet be in place on (and/or in) the bone, thereby eliminating the risk of damaging the female fastener while forming the hole. The hole may be of uniform diameter, allowing the hole to be bored through both bone fragments in a single-step drilling process from only one of the opposite sides of the bone. Alternatively, the hole may include a bore and a counterbore, which may be drilled from respective opposite sides of the bone. The hole diameter may be large enough such that a gliding hole is formed, which allows the male fastener to be inserted translationally into the hole with little or no resistance. The formation of a gliding hole permits compressive force to be applied across the fracture by the fastener assembly when the fastener assembly is tightened against opposite sides of the bone.

Once the hole is formed through both fragments of the bone, the female fastener may be inserted and secured in the clamping instrument. An insertion tool that mates with the clamping instrument may carry the female fastener into the clamping instrument and restrict its movement therein. The insertion tool may be locked to the clamping instrument by a cross bar or other locking device.

The same clamping instrument may be used to guide a gauge for measuring the distance across the bone at the hole. The measured distance can guide the selection of an appropriate length of male fastener.

The male fastener then can be inserted into the hole in bone from the clamping instrument and into locked engagement with the female fastener. In some embodiments, the fasteners may lock to one another by threaded engagement. The fasteners may have complementary, preformed threads to produce the threaded engagement, or the threaded engagement may result from material deformation (e.g., of the female fastener) as the male fastener is advanced into the female fastener. The material deformation may be caused by an external thread of the male fastener, which may form a complementary internal thread in the female fastener. The female fastener may be open-ended, allowing the male fastener to extend completely through the female fastener and protrude therefrom (away from the bone) as far as desired. More particularly, the male fastener may be adjusted to at least substantially maintain the level of compression applied by the clamping instrument and, optionally, to apply additional compression to the fracture.

In some embodiments, prior to tissue incision, the clamping instrument is used in conjunction with a pair of removable marking accessories. The marking accessories may be urged against a subject's skin to mark locations where incisions are to be made to access opposite sides of the subject's fractured bone.

Further aspects of the present disclosure are described in the following sections: (I) overview of bone fixation systems, (II) methods of fixing bone, (III) composition of a fastener assembly, and (IV) examples.

I. Overview of Bone Fixation Systems

Figure 2:
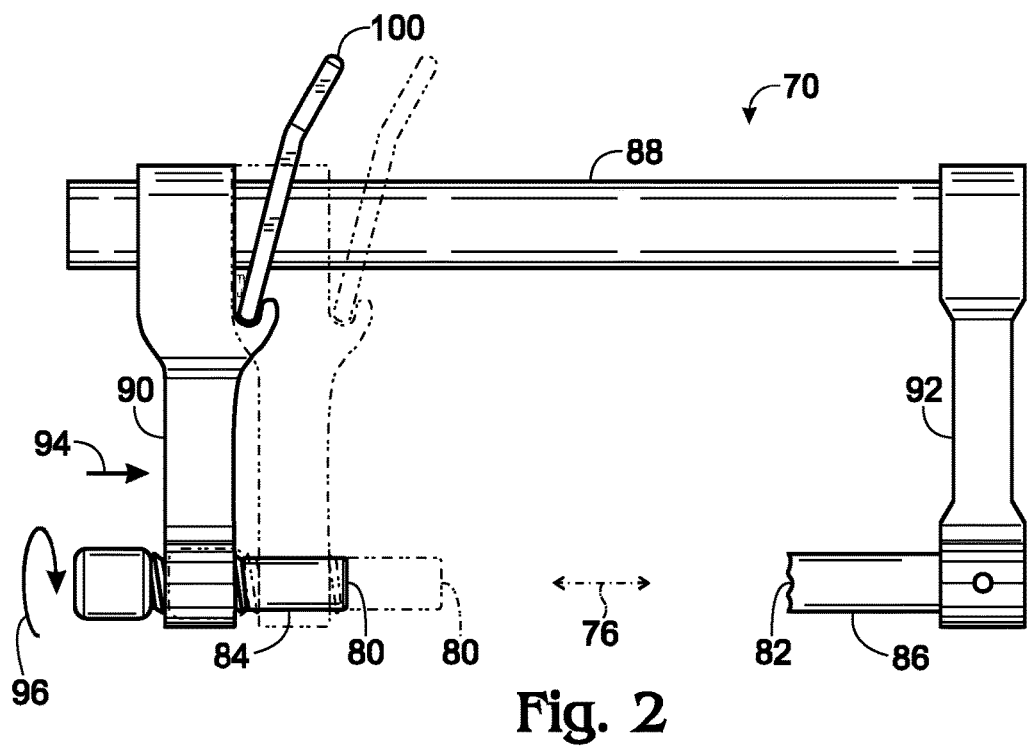
FIG. 2 is an elevational view of the clamping instrument of FIG. 1 and illustrates translational and rotational manipulation to adjust the distance between a pair of jaws of the clamping instrument, in accordance with aspects of the present disclosure.
Figure 3:
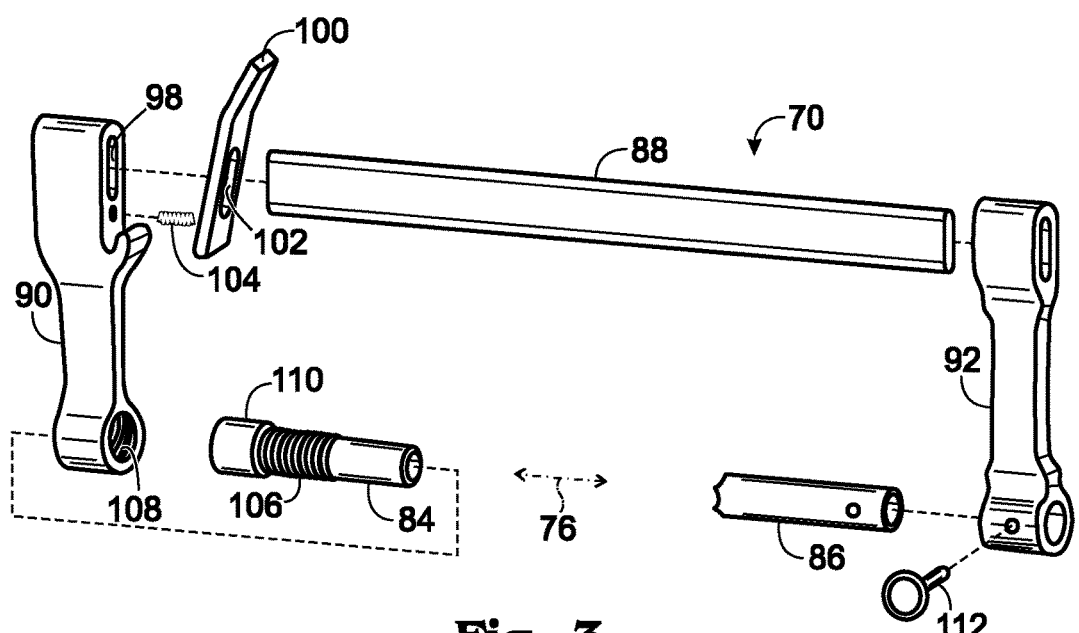
FIG. 3 is an exploded view of the clamping instrument of FIG. 1.

This section provides an overview of exemplary bone fixation systems of the present disclosure, as illustrated by bone fixation system 50; see FIGS. 1-3.

System 50 utilizes a fastener assembly 51 including a pair of fasteners 52, 54 that are implanted in a subject to fix a bone 56 (see FIG. 1). The fasteners may attach to one another by threaded engagement to form a locked fastener assembly that extends in a direction across the bone, while spanning at least one discontinuity in the bone, such as at least one fracture 58. The fasteners may be described as a first fastener and a second fastener. The first or second fastener may be a male fastener having an external thread, and the other fastener may be a female fastener defining an opening to receive a leading end portion of the male fastener, and particularly at least a portion of the male fastener's external thread. The female fastener may or may not have a preformed, complementary internal thread at the opening.

Fastener 52 may be an elongated male fastener having a head 60 and an externally threaded shaft 62. The head may define an interface for a driver and may be enlarged in cross-section relative to the shaft to stop advancement of male fastener 52 into bone 56. The interface may include external facets or a recess, among others. At least a leading end 64 of shaft 62 may be threaded externally, although any suitable axial portion or substantially the entire length of shaft 62 may be threaded externally. The length of male fastener 52 alone, and/or the length of fastener assembly 51 when the fasteners are attached to one another, may be sufficient to span bone 56 where the male fastener is installed.

Fastener 54 may be a female fastener configured to receive a portion of shaft 62, such as a leading end 64 thereof. Accordingly, female fastener 54 may define a hole 66 (e.g., a through-hole or blind hole) that leading end 64 extends into and/or through when the fasteners are attached to one another. Hole 66 may have a preformed internal thread that is complementary to an external thread of male fastener 52, or may be deformed by the external thread to create an internal thread as the fasteners are being attached to one another. To facilitate this deformation, at least a portion of the female fastener defining hole 66 may be softer and/or more deformable than the male fastener. For example, male fastener 52 may be composed of a harder metal and female fastener 54 (or at least a wall of hole 66) of a softer metal, or the male fastener may be composed of metal and the female fastener (or at least a wall of hole 66) of polymer (e.g., PEEK). In other embodiments, the male fastener may be deformed by an internal thread of the female fastener to create an external thread on the male fastener as the fasteners are being attached to one another.

The female fastener may be configured to be placed on and/or in bone 56. In the depicted embodiment, the female fastener functions as a nut that remains outside the bone. The nut has a noncircular cross-section, such as created by external facets, that can be engaged during installation to prevent rotation, as described further below. In other embodiments, the female fastener enters bone 56 partially or completely (e.g., see Example 1). For example, the female fastener may include a barrel that is placed into bone. The barrel may be nonthreaded externally, or may include an externally-threaded barrel that can be driven rotationally into the bone via a driver interface, for threaded engagement with the bone. The interior of the barrel may have a preformed internal thread, or an internal thread may be created by the male fastener through deformation, as described above.

The fastener assembly optionally includes one or more washers 68a, 68b. Male fastener 52 may extend through each washer or through only a subset of the washers. Each washer may be disposed in engagement with one of fasteners 52, 54 and with bone 56. For example, the washers when installed may be disposed on opposite sides of the bone, with washer 68a located between head 60 and the bone, and washer 68b located between female fastener 54 and the bone.

System 50 also includes a clamping instrument 70 to facilitate installation of the fastener assembly (see FIG. 1). The clamping instrument can be manipulated to apply compressive force to bone 56, which may reduce fracture 58, attach instrument 70 to the bone, and provisionally clamp pieces 72, 74 of the bone against one another to hold them in place while the fastener assembly is being installed. The clamping instrument also may define an axis 76 on which fastener installation occurs, indicated by arrows at 78, and may provide mating sites for various removable accessory components of the instrument.

FIG. 2 shows clamping instrument 70 before (solid lines) and after (dash-dot-dot lines) an exemplary adjustment to attach the instrument to bone. The adjustment changes a distance (also called a spacing or separation) between a pair of jaws 80, 82 of the instrument. Each jaw may be provided by a respective tube 84, 86 and may be configured to engage bone (and/or to engage a device, such as a bone plate, located on the bone). The tubes may be arranged coaxially with one another on axis 76, such that the axis extends through both jaws and centrally through each tube. Each tube (and/or a jaw thereof) may be connected to an elongated, linear frame member (e.g., a bar 88) via a respective arm 90, 92. At least one of arms 90, 92 may be configured to slide along bar 88, to adjust the distance between the jaws by translational motion, indicated by a motion arrow at 94, parallel to axis 76. In the depicted embodiment, arm 90 is movable and arm 92 is fixed. At least one of tubes 84, 86 also may be movable with respect to its corresponding arm, to further adjust the distance between the jaws, optionally by rotational motion, indicated by a motion arrow at 96. In the depicted embodiment, tube 84 is in threaded engagement with, and movable with respect to, movable arm 90, and tube 86 is fixed with respect to fixed arm 92. In other embodiments, fixed arm 92 may support a movable tube and movable arm 90 may support a fixed tube.

Translational motion 94 may provide a coarse adjustment, with a larger permitted range of net displacement parallel to axis 76, while rotational motion 96 may provide a fine adjustment, with a smaller permitted range of the net displacement. To attach the clamping instrument to bone, jaws 80, 82 may be placed against opposite sides of a bone by translational motion of the jaws relative to one another, and then further tightened against the bone by rotational motion of the jaws relative to one another.

FIGS. 2 and 3 show further aspects of clamping instrument 70. Movable arm 90 may define a channel 98 through which bar 88 extends. The channel may be sized to permit smooth travel of the arm along the bar without substantial wobble or transverse play, such that tubes 84, 86 remain coaxial with one another as the distance between the jaws is adjusted.

Translational motion of movable arm 90 may be controlled by a locking member 100, which may have a restrictive (locking) configuration and a permissive configuration. The locking member may be manipulated manually to move the locking member from the restrictive configuration to the permissive configuration. In the restrictive configuration, the locking member prevents translational motion of jaws 80, 82 (and/or tubes 84, 86) relative to one another in at least one of two opposite directions parallel to axis 76. For example, in the depicted embodiment, locking member 100 selectively prevents movement of the jaws away from one another, to increase the distance between the jaws, while permitting movement of the jaws toward one another, to decrease the distance between the jaws. In the permissive configuration, the locking member permits relative translational motion of the jaws in either of the opposite directions, to increase or decrease the distance between the jaws as desired.

Locking member 100 may be configured to engage bar 88 in an orientation-dependent manner (see FIG. 3). The locking member may define an aperture 102 sized in correspondence with the width of bar 88, such that bar 88 can extend through the aperture. A base of the locking member may be attached to arm 90, with the locking member cantilevered from the arm and oriented obliquely with respect to bar 88 in the restrictive configuration of FIG. 2. In this orientation, the bar is engaged by a wall of aperture 102. The locking member may be biased toward the restrictive configuration, relative to the permissive configuration, by a biasing member 104, such as a spring. If the jaws are urged toward one another translationally, to decrease the distance between the jaws, the locking member is encouraged to move toward the permissive configuration (more orthogonal with respect to bar 88, counterclockwise in FIG. 2). This decreases friction between the locking member and the bar, thereby permitting motion. In contrast, if the jaws are urged away from one another, in an attempt to increase the distance between the jaws, the locking member is encouraged to move clockwise in FIG. 2 and into tighter frictional engagement with the bar, thereby preventing motion. When the user wants to release the clamp, the locking member can be engaged manually near the top thereof, and moved to the permissive configuration.

In other embodiments, the locking member may have a restrictive configuration that blocks translational motion non-selectively in opposite directions parallel to axis 76. For example, the locking member may be a locking bolt having a threaded connection to arm 90. The locking bolt may be advanced tightly against bar 88 by rotation, to fix the position of the arm on the bar, and retracted by rotation to permit the arm to slide along the bar.

Fixed arm 92 may be attached firmly to tube 86 and bar 88. For example, the fixed arm may be attached to either or both elements by welding, a press-fit, fasteners, or the like.

Rotatable tube 84 may thread into movable arm 90 from the outer side of the arm (see FIG. 3). Tube 84 may have an external thread 106 that engages an internal thread 108 formed inside the arm. The tube may have a graspable head 110 of increased diameter, to facilitate manual manipulation of the tube and to stop rotational advancement of the tube toward the other tube through contact between head 110 and arm 90.

Clamping instrument 70 may be configured to receive a locking member, such as a locking pin 112, in aligned holes of fixed tube 86 and fixed arm 92. The function of the locking pin is described below in Section II.

Further aspects of bone fixation system 50 are described elsewhere herein, such as in Sections II-IV. Example 1 of Section IV describes another exemplary bone fixation system 150 that illustrates various modifications to system 50.

II. Methods of Fixing Bone

This section describes exemplary methods of fixing bone with the systems of the present disclosure; see FIGS. 4-15. The method steps of this section may be performed in any suitable order and combination, using any suitable combination of the system components of the present disclosure.

A bone may be selected for fixation. The bone may be a long bone. Exemplary bones that may be suitable include an arm bone (e.g., a humerus, radius, or ulna), or a leg bone (e.g., a femur, tibia, or fibula), among others. The bone may have at least one discontinuity, such as at least one break, cut, nonunion, a combination thereof, or the like, or may need to be stabilized for any other reason. The discontinuity may, for example, be oriented at least generally parallel, obliquely, or at least generally orthogonal to the long axis of the bone. Any suitable region of the bone may be selected for fixation with the fastener assembly disclosed herein. In other words, the fastener assembly may be installed in the shaft of the selected bone (e.g., to fix a mid-shaft fracture) or near the proximal or distal end of the bone (e.g., to fix a metaphyseal and/or intra-articular fracture). The fastener assembly when installed may span the discontinuity or may attach another fixation device (such as a bone plate) to the bone, and the fixation device may span the discontinuity.

FIGS. 4-8 and 10-15 illustrate exemplify configurations that may be produced by performance of the methods of the present disclosure on a fractured tibia as selected bone 56.

Figure 4:
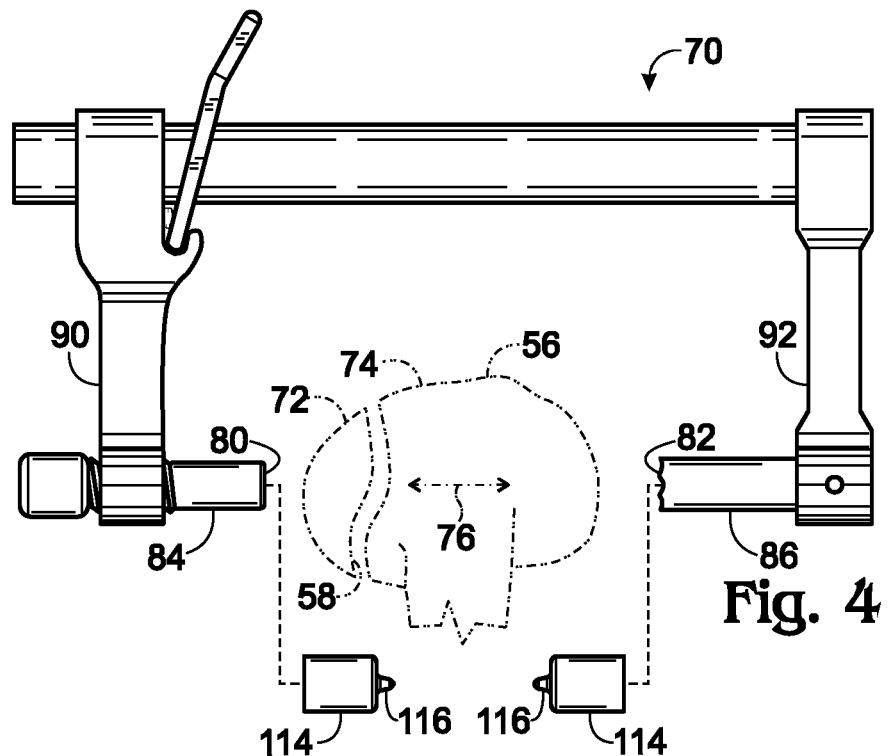
FIG. 4 is an elevational view of the clamping instrument of FIG. 1, taken in the presence of a pair of connectable marking accessories to mark respective locations at which skin incisions can be created to access opposite sides of a bone, with the accessories exploded from their operative sites on the clamping instrument, in accordance with aspects of the present disclosure.
Figure 5:
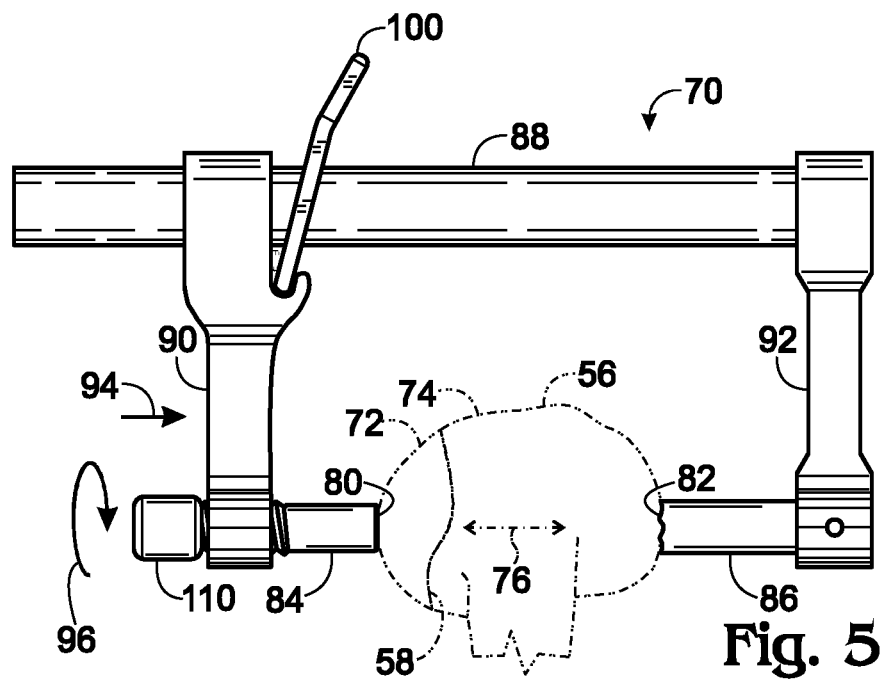
FIG. 5 is an elevational view of the clamping instrument and bone of FIG. 4, taken with jaws of the instrument engaged with opposite sides of the bone and applying compressive force to the bone to reduce a fracture thereof, in accordance with aspects of the present disclosure.

Regions of soft tissue (e.g., skin) covering opposite sides of bone 56 and disposed on a desired, prospective fastener placement axis 76 may be marked using clamping instrument 70 (see FIG. 4). The marked regions define sites at which incisions can be created with a cutting tool (e.g., a scalpel) to access underlying surface regions of the bone. Soft tissue can be marked by direct contact with at least one of jaws 80, 82 and/or by contact with at least one marking member 114. In the depicted embodiment, a pair of marking members 114 may be mated with respective tubes 84, 86 to cover jaws 80, 82. Each marking member may be hollow, to receive an end portion of one of the tubes, and may have an inner diameter sized in correspondence with the outer diameter of the corresponding tube, to provide a close fit that connects the marking member to the tube by friction. The marking member thus may be a cap that adds a protrusion, such as a spike 116, to the end of one of the tubes. The protrusion may be located on axis 76. To mark soft tissue, the distance between jaws 80, 82 is decreased until the jaws or the marking members are pushed tightly against the soft tissue, to create indentations or puncture sites. The distance between the jaws is then increased, to facilitate removal of the clamping instrument, and marking members 114 are taken off tubes 84, 86.

Clamping instrument 70 may be engaged with opposite surface regions of bone 56 using jaws 80, 82 (see FIG. 5), after these surface regions have been accessed via incisions. Arms 90, 92 may be urged toward one another to reduce the distance between jaws 80, 82 via translational motion 94 until both jaws contact bone 56. This adjustment of the distance between the jaws may be performed without any manipulation of locking member 100, or the locking member may be manipulated to allow arm 90 to move freely (or more freely) along bar 88. The distance between the jaws may be further or alternatively adjusted by turning tube 84 about axis 76, indicated at 96, to tighten the jaws against bone 56. The tube may be turned manually via head 110, or with a tool such as a wrench (see Example 1). Either or both translational/rotational adjustments of the distance between the jaws may move bone pieces 72, 74 toward and against one another, and into closer approximation to the original, relative anatomical positions of the bone portions forming the pieces, to reduce the fracture (compare FIGS. 4 and 5).

Figure 6:
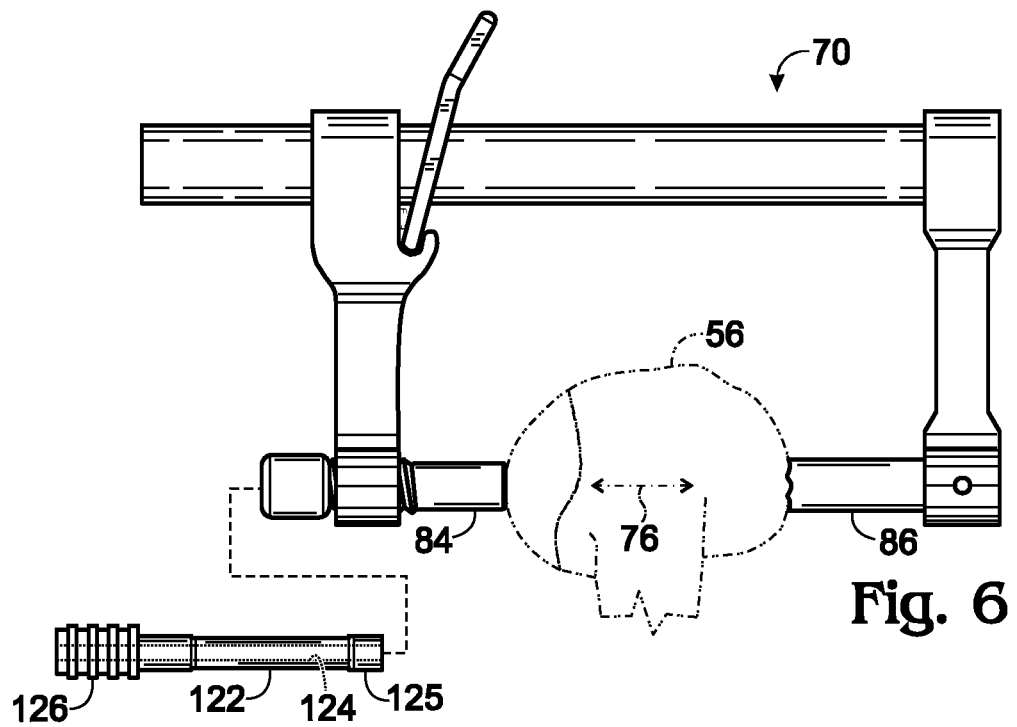
FIG. 6 is an elevational view of the clamping instrument and bone of FIG. 5, taken in the presence of a guide member that mates with the clamping instrument to define a guide path for a boring tool to form a hole through the bone, with the guide member exploded from its operative site in the clamping instrument, in accordance with aspects of the present disclosure.
Figure 7:
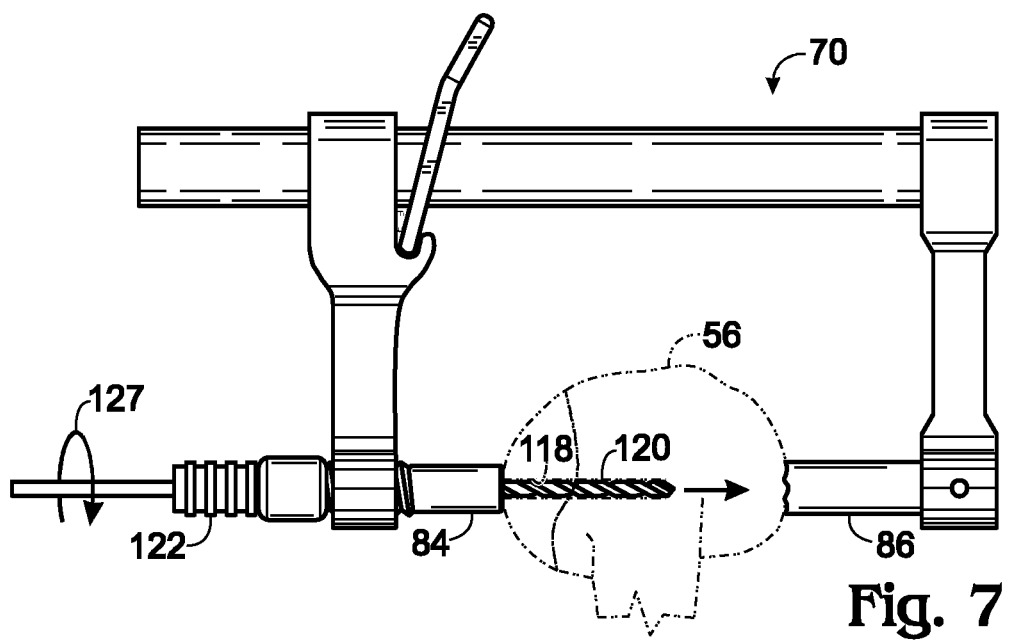
FIG. 7 is an elevational view of the clamping instrument, guide member, and bone of FIG. 6, taken after the guide member has been operatively mated with the clamping instrument and while the guide member is guiding a boring tool along a drilling path through the bone, in accordance with aspects of the present disclosure.

A hole 118 (also called a bore) may be created through bone 56 on axis 76 with a boring tool 120 (also called a drill) (see FIGS. 6-8). The hole may be created by advancing boring tool 120 into bone 56 from tube 84. In embodiments where the female fastener will be disposed at least partially in bone 56, a counterbore to receive the female fastener on the far side of the bone may be formed by advancing a boring tool of larger diameter than tool 120, into bone 56 on axis 76 from tube 86 (see Example 1).

FIG. 6 shows a guide member 122 structured as a cannula to direct boring tool 120 along axis 76. The guide member defines a channel 124 having a diameter corresponding in size to the outer diameter of boring tool 120. Tube 84 of instrument 70 defines a passage corresponding in diameter to an outer diameter of a shaft 125 of guide member 122. Accordingly, the guide member can be mated with clamping instrument 70 by placing shaft 125 into tube 84. A head 126 of the guide member may stop advancement of the guide member into tube 84, and provides a site at which the guide member can be grasped manually.

FIG. 7 shows boring tool 120 creating hole 118. The boring tool is being rotated, indicated at 127, and pushed into bone 56. Boring is complete when the leading end of the boring tool passes through the far side of bone 56 and enters tube 86. The diameter of the hole may be larger than the outer diameter of the shaft of the male fastener, to produce a gliding hole that allows the male fastener to be placed easily into the hole without substantial rotation (or threaded engagement with bone).

FIG. 8 shows hole 118 extending through bone 56, and boring tool 120 retracted and removed from guide member 122. Female fastener 54 now may be placed on the installation axis, at the far end of hole 118, without any risk of damage by boring tool 120. The design of clamping instrument 70 may permit female fastener 54 to be placed in position for attachment to male fastener 52, while the clamping instrument remains attached to bone 56.

The female fastener may be carried into position by an insertion tool 128 (see FIGS. 8 and 9). The insertion tool may have a shaft 130 and a head 132. The leading end (also called the inner end) of shaft 130 opposite head 132 may define a receiver 134 for female fastener 54. The receiver may be complementary in shape to the female fastener, to restrict rotation and axial motion thereof. Shaft 130 may be sized to be mated with tube 86 by insertion therein. Corresponding holes 136, 137 may be defined by shaft 130 and arm 92.

FIG. 10 shows insertion tool 128 mated with tube 86 and locked with pin 112 (also see FIG. 3). The pin may extend through aligned holes 136, 137 to prevent rotation and axial motion of insertion tool 128 (and thus female fastener 54) (also see FIG. 8). The female fastener is arranged coaxially with hole 118.

In some embodiments, as described in Example 1, a counterbore may be formed at the far end of hole 118, to receive a female fastener. In these embodiments, the female fastener may be placed at least partially into bone 56, on axis 76. Formation of the counterbore may be guided by tube 86 and/or a cannulated guide member mated with the tube.

Figure 11:
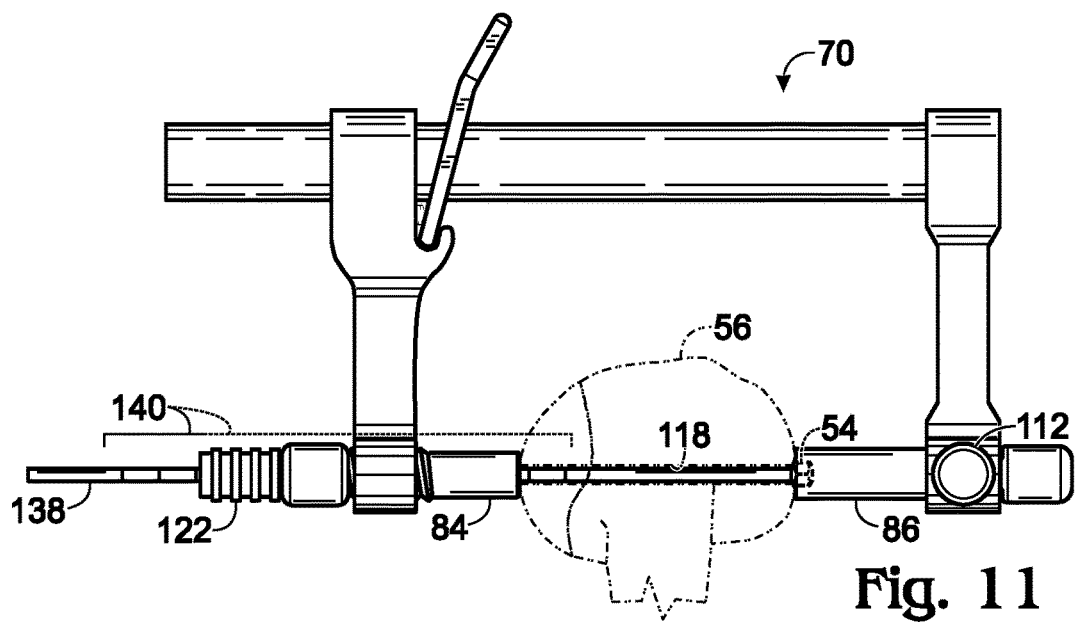
FIG. 11 is an elevational view of the clamping instrument, guide member, female fastener, insertion tool, depth gauge, and bone of FIG. 10, taken with the depth gauge fully inserted into the hole and stopped by contact with the female fastener, in accordance with aspects of the present disclosure.

A depth/length of hole 118 may be measured with a depth gauge 138, to allow selection of a suitable size (i.e., length) of the male fastener or the fastener assembly (see FIGS. 10 and 11). The depth gauge may be an elongated member (e.g., a rod or bar) that is smaller in diameter than boring tool 120, which allows the depth gauge to be freely advanced into hole 118 from guide member 122. The depth gauge may have a series of indicia 140 (also called reference marks) each corresponding to a different depth/length of hole 118 (and different length of male fastener). The depth gauge may be inserted into hole 118 until the gauge is stopped by contact with female fastener 54. One or more indicia 140 visible when the depth gauge is fully inserted can be noted to determine the depth of hole 118 (i.e., the distance between opposite ends of the hole) and/or a suitable size of male fastener.

Figure 12:
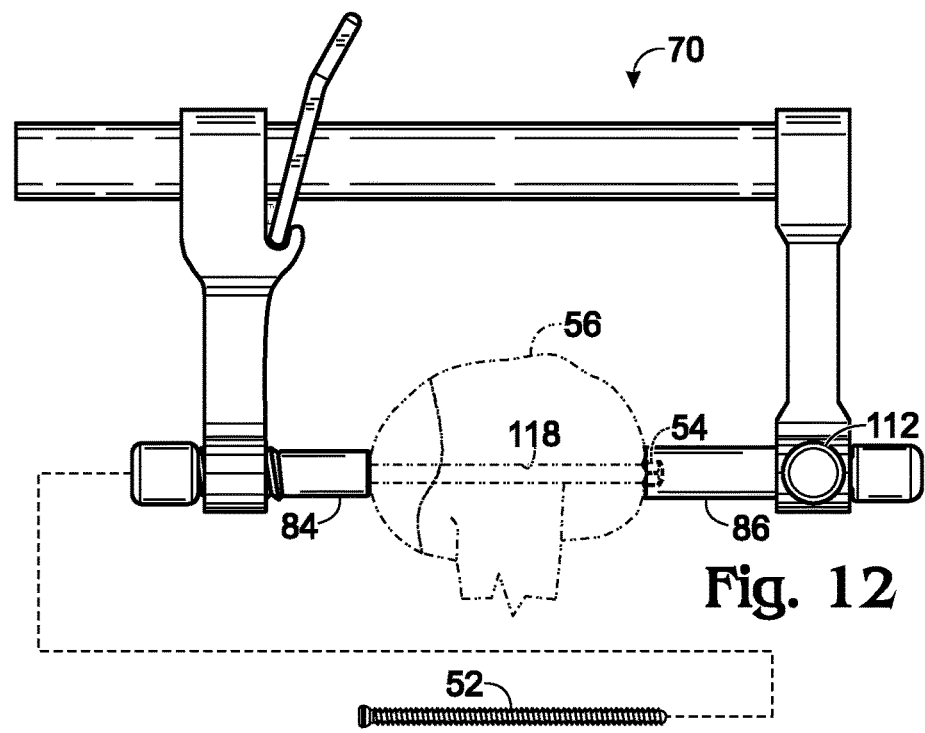
FIG. 12 is an elevational view of the clamping instrument, female fastener, insertion tool, and bone of FIG. 11, taken after removal of the depth gauge and the guide member and in the presence of a male fastener, with the male fastener exploded from its inserted position, in accordance with aspects of the present disclosure.

Clamping instrument 70 can be readied to guide male fastener 52 into hole 118 (see FIG. 12). Guide member 122 and depth gauge 138 may be removed. A suitable length of male fastener may be selected based on a reading from the depth gauge.

Figure 13:
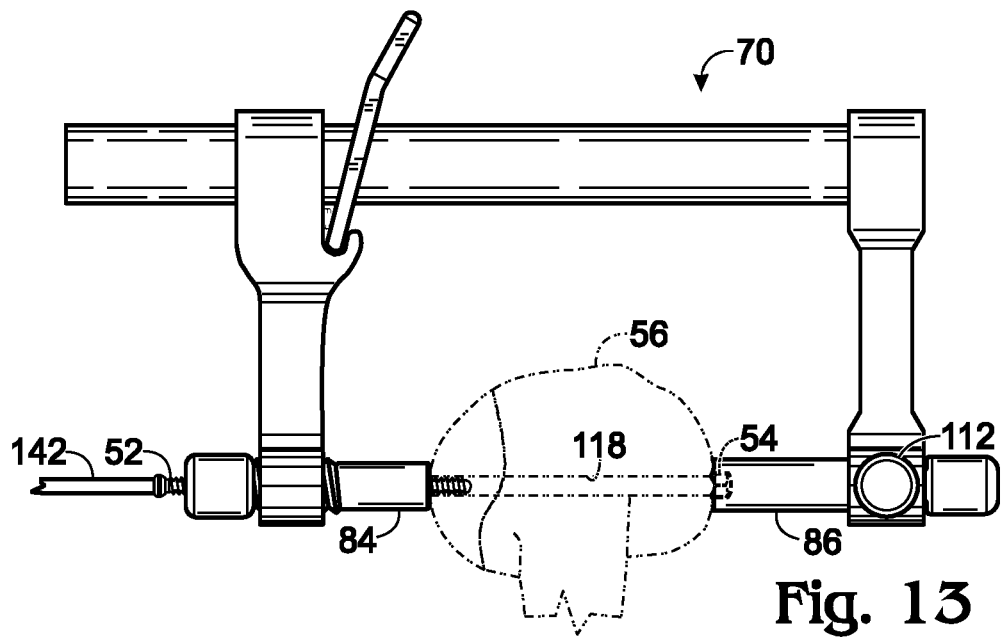
FIG. 13 is an elevational view of the clamping instrument, female fastener, insertion tool, male fastener, and bone of FIG. 12, taken as the male fastener is being advanced into the bone by a driver, in accordance with aspects of the present disclosure.
Figure 14:
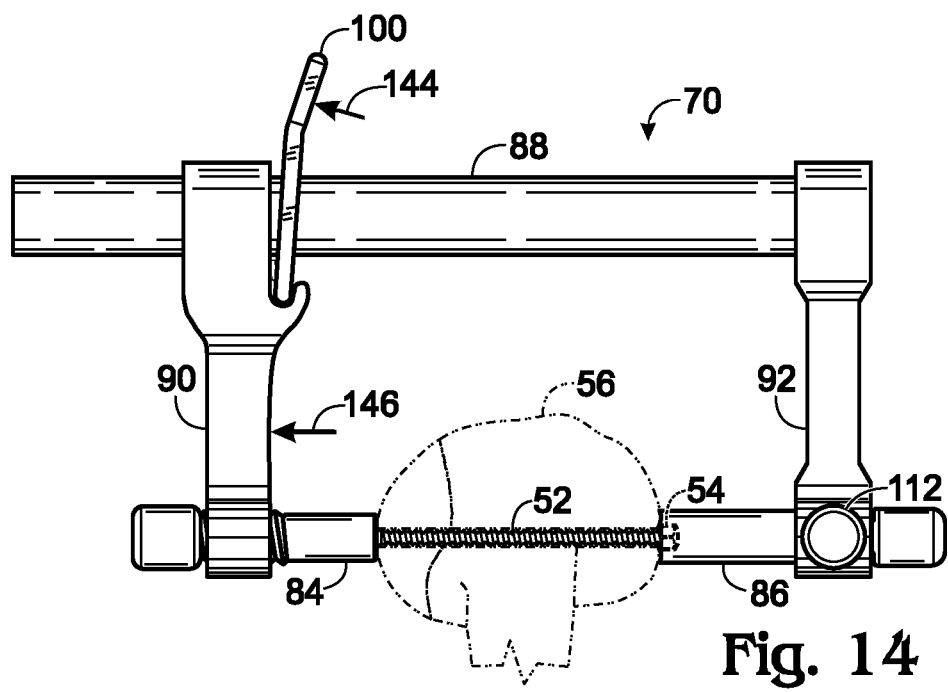
FIG. 14 is an elevational view of the clamping instrument, female fastener, insertion tool, male fastener, and bone of FIG. 13, taken after the male fastener and the female fastener have been attached to one another and tightened against the bone, and with the clamping instrument in a released configuration that allows jaws thereof to be moved away from one another without rotation, in accordance with aspects of the present disclosure.

Male fastener 52 may be placed into hole 118 via tube 84 (see FIGS. 13 and 14). A suitable driver 142 may be engaged operatively with the trailing end of the male fastener to urge the male fastener axially, optionally without any rotation, until the male fastener reaches female fastener 54. Driver 142 may be used to turn male fastener 52 when the fasteners are in contact, to encourage threaded advancement of the leading end of the male fastener into the female fastener. The male fastener may be turned until the fastener assembly applies a desired amount of compression to bone 56. When the fastener assembly is fully installed, male fastener 52 may or may not protrude from female fastener 54.

Figure 15:
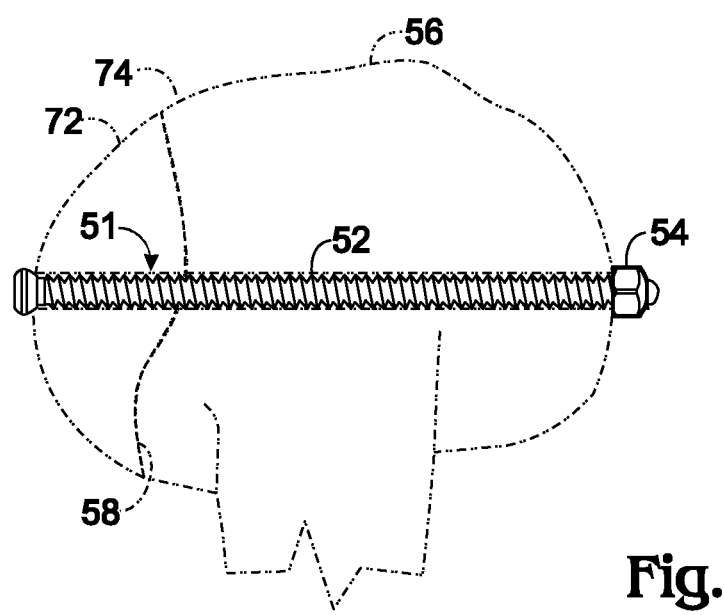
FIG. 15 is a view of the female fastener, male fastener, and bone of FIG. 14, taken after removal of the clamping instrument.
Figure 16:
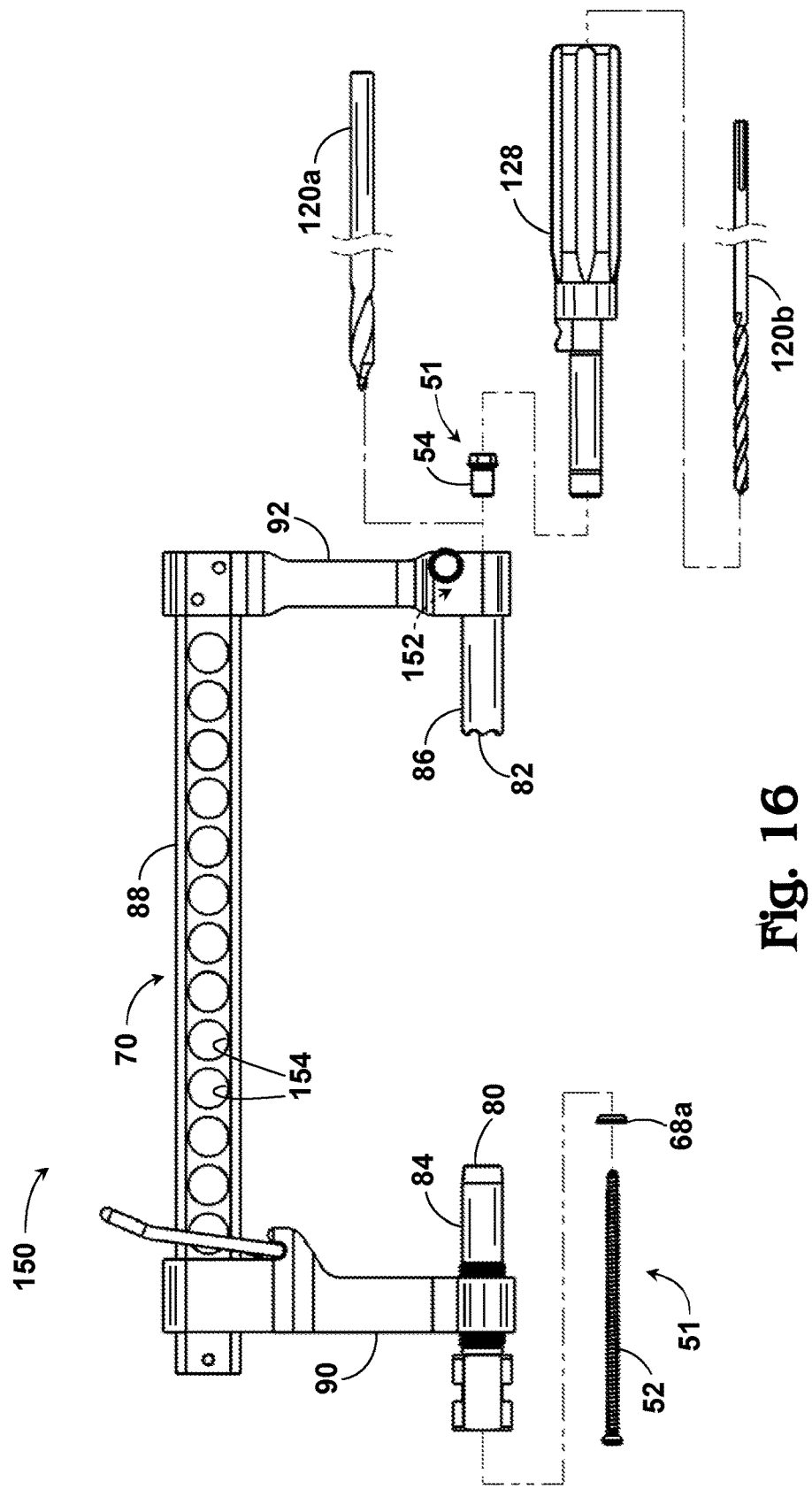
FIG. 16 is an exploded view of selected components of another exemplary bone fixation system, in accordance with aspects of the present disclosure.

Clamping instrument 70 may be removed from bone 56 (see FIGS. 14 and 15). Locking member 100 may be placed into a permissive configuration by applying a force 144 that moves the locking member to a more orthogonal orientation. While the locking member is held in the permissive configuration, a force 146 may be applied to arm 90 that causes the arm to slide along bar 88 in a direction away from arm 92.

III. Composition of a Fastener Assembly

The fasteners of the fastener assembly may have any suitable composition. Each fastener may be formed of any suitable biocompatible material(s) and/or bioresorbable (bioabsorbable) material(s). Illustrative biocompatible materials that may be suitable include (1) metal (for example, titanium or titanium alloy, cobalt-chrome alloy, stainless steel, etc.); (2) polymer/plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer/plastic (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); or (4) any combination thereof, among others.

IV. Examples

The following examples describe further exemplary aspects and features of the bone fixation systems and methods of the present disclosure. These examples are intended for illustration and should not limit or define the entire scope of the present disclosure.

Example 1. Exemplary Bone Fixation System with an in-Bone Female Fastener

This example describes an exemplary bone fixation system 150 that illustrates exemplary modifications to system 50 of Sections I and II, such as a fastener assembly 51 including a female fastener 54 that is placed partially in bone; see FIGS. 16-28. Any suitable combination of features of system 150 may be introduced into system 50, and vice versa, and any of the methods of the present disclosure may be performed with system 50, system 150, or a hybrid of systems 50 and 150.

System 150 has and/or enables the following differences from system 50. Drilling may create a bore and a counterbore in the bone that collectively extend through the bone. The counterbore and bore may be formed by respective different drill bits 120*a*, 120*b* of different outer diameter in separate drilling steps, or may be performed in one drilling step with a stepped drill. All drilling may be performed through tube 86 (i.e., from female fastener 54 side of the bone), or the bore may be drilled through tube 84 (i.e., from male fastener 52 side of the bone) and the counterbore through tube 86. Female fastener 54 of system 150 extends into the bone when installed and occupies the counterbore drilled in the bone. The female fastener may have a head with a tapered hex geometry such that the fastener is retained more reliably by insertion tool 128. Also, insertion tool 128 may be cannulated so that it can also be used as a drill guide for drill bit 120*b*. The insertion tool may be locked to the clamping instrument with a built-in, spring-loaded locking mechanism 152. These and other modifications to system 50 are described further below.

Clamping instrument 70 of system 150 has various differences from that of system 50. For example, bar 88 defines a series of holes 154 to make the instrument lighter. Also, male-side tube 84 is configured to be turned with a wrench, if needed, as described further below.

FIGS. 17 and 18 show respective side and end views of female fastener 54 for fastener assembly 51. Female fastener 54 may have a barrel 156, a flange 158, and a head 160, and defines axial through-hole 66. Barrel 156 is configured to be received in a counterbore formed in bone by drill bit 120*a* (see FIG. 16), and may have a smooth cylindrical exterior. Flange 158 protrudes radially outward and has a larger diameter than the barrel. The flange is configured to engage the outside surface of bone, to prevent entry of the female fastener past the barrel into the counterbore. Head 160 has mating structure, such as external flats 162 and/or or one or more recesses, for mating with a complementary mating structure of insertion tool 128. In the depicted embodiment, the head has six flats 162 to produce a hexagonal geometry, although a different number of flats and/or another geometry may be suitable. The head may taper gradually away from barrel 156, as shown, such that the head wedges slightly into the insertion tool when they are mated, to allow the insertion tool to retain the female fastener more effectively. In other embodiments, head 160 may be absent and the mating structure may be produced by a suitably shaped recess formed at the outer end of through-hole 66.

FIGS. 19-21 show male-side tube 84 of system, which is generally similar to tube 84 of system 50. The tube has a head 110 and a shaft. An external thread 106 is formed on the shaft. An axial channel 164 extends through the tube, and gives the tube an inner diameter that is larger than the maximum diameter of male fastener 52 and washer 68*a*, allowing both to pass axially through the tube. Head 110 of tube 84 of system 150 can be grasped and manipulated by hand, but also has flats 166 that facilitate turning the tube with a wrench, such as an open-end wrench, if desired or necessary for tightening or removal.

Figure 22:
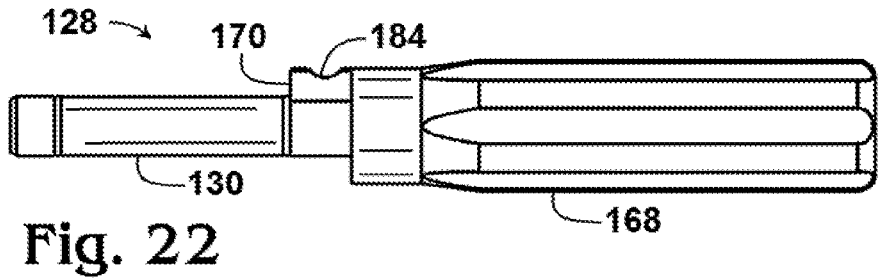
FIG. 22 is an elevational view of an insertion tool of the bone fixation system of FIG. 16.
Figure 23:
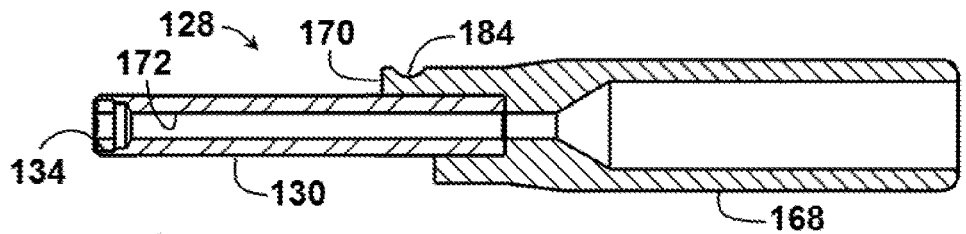
FIG. 23 is a longitudinal sectional view of the insertion tool of FIG. 22.
Figure 24:
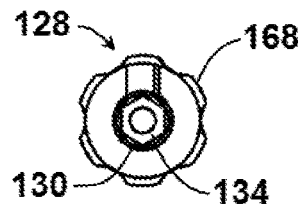
FIG. 24 is an inner end view of the insertion tool of FIG. 22.

FIGS. 22-24 show insertion tool 128 of system 150 in more detail. The insertion tool has a shaft 130, a handle 168, and a key 170. The key is described in more detail below with respect to locking mechanism 152 of the clamping instrument.

Insertion tool 128 may define an axial channel 172 that extends through the tool from end to end. Channel may form a receiver 134 for female fastener 54 at the distal (inner) end of the insertion tool. Receiver 134 may be complementary to a portion of the female fastener, such as head 160 thereof (see FIG. 17). Accordingly, the receiver may define a recess having a plurality of planar wall (e.g., six in the depicted embodiment). Channel 172 may have a minimum diameter that substantially matches the outer diameter of drill bit 120*b*, such that the drill bit can be guided by the channel into bone with little or no wobble. Channel 172 may widen proximally in handle 168, with a taper connecting the wider and narrower portions of the channel. The taper may help to center the drill bit in the channel as the drill bit is being advanced to the narrower portion of the channel in shaft 130.

Figure 25:
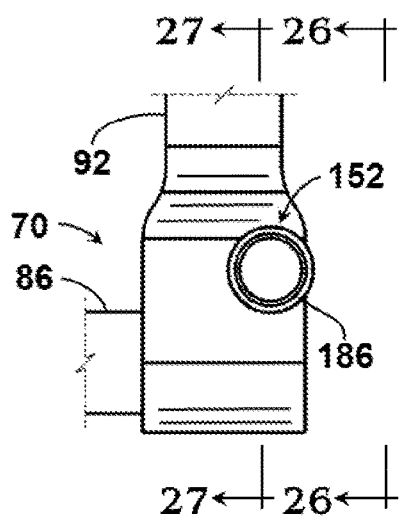
FIG. 25 is a fragmentary elevational view of the clamping instrument of the bone fixation system of FIG. 16, taken generally around the junction between the frame and one of the tubes of the clamping instrument, where the insertion tool of FIG. 22 locks to the frame.
Figure 26:
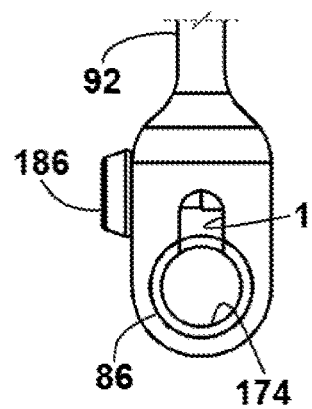
FIG. 26 is a fragmentary end view of the clamping instrument of FIG. 25, taken generally along line 26-26 of FIG. 25.
Figure 27:
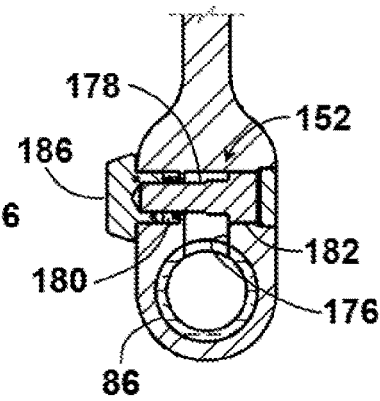
FIG. 27 is a fragmentary sectional view of the clamping instrument of FIG. 25, taken generally along line 27-27 of FIG. 25.

FIGS. 25-27 show a fragmentary portion of clamping instrument 70 of system 150, taken around female-side tube 86 and locking mechanism 152. Tube 86 defines a channel 174 having a diameter that substantially matches the diameter of larger drill bit 120*a*. Accordingly, tube 86 can guide drill bit 120*a* into bone with little or no wobble. The inside diameter of tube 86 is larger than the maximum diameter of female fastener 54, which allows the female fastener to pass through the tube axially. The inside diameter of tube 86 also substantially matches the outer diameter of shaft 130 of insertion tool 128, such that the shaft fits closely in the tube. Key 170 of the insertion tool is received in a corresponding recess 176 defined by female-side arm 92 of clamping instrument 70, as the insertion tool is assembled with the clamping instrument. The key prevents rotation of the insertion tool about its long axis.

Insertion tool 128 can be locked to arm 92 of the clamping instrument using locking mechanism 152. The locking mechanism includes a retainer 178 that is biased toward a locking position with a spring 180. In the locking position, a retaining region 182 of the retainer is received in an indentation 184 of key 170, to prevent removal of the insertion tool from tube 86 (also see FIGS. 22 and 23). Manual pressure on a button 186 of the retainer compresses the spring and urges retaining region 182 out of indentation 184, to produce the releasing position shown in FIG. 27. The releasing position allows the insertion tool to be withdrawn axially from tube 86.

Figure 28:
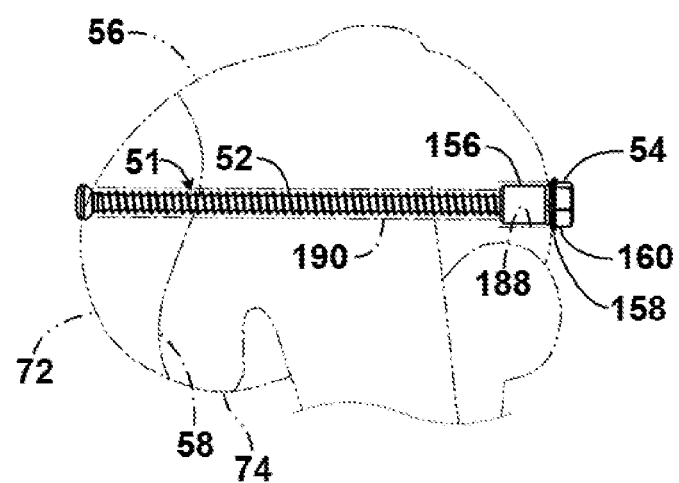
FIG. 28 is a view of the fastener assembly of the bone fixation system of FIG. 16 installed in bone.

FIG. 28 shows fastener assembly 51 installed in bone 56 after removal of clamping instrument 70. Barrel 156 of female fastener 54 is located in a counterbore 188 drilled in the bone with drill bit 120*a*. Flange 158 is engaged with an outer surface region of the bone, and hexagonal head 160 is located outside the bone. Male fastener 52 extends through a bore 190 formed by drill bit 120*b*.

Example 2. Selected Embodiments

The following paragraphs describe selected embodiments of the present disclosure. These embodiments are intended for illustration only, and should not limit the entire scope of the present disclosure.

Paragraph 1. A method of fixing bone, the method comprising, in any order: (A) compressing a bone with jaws of a clamping instrument, such that the clamping instrument is attached to the bone, wherein a distance between the jaws is adjustable independently by translational motion and rotational motion of the jaws relative to one another; (B) creating a hole through the bone on an axis extending through each of the jaws; (C) placing a male fastener into the hole; and (D) attaching a female fastener to a leading end of the male fastener.

Paragraph 2. The method of paragraph 1, wherein the step of compressing a bone includes a step of engaging opposite sides of the bone with the jaws.

Paragraph 3. The method of paragraph 2, wherein the step of engaging opposite sides of the bone includes a step of disposing respective tubes adjacent the opposite sides of the bone, and wherein the axis extends along a central through-axis of each respective tube.

Paragraph 4. The method of any of paragraphs 1 to 3, wherein the clamping instrument includes a locking member configured to selectively restrict translational motion of the jaws away from one another while permitting translational motion of the jaws toward one another.

Paragraph 5. The method of paragraph 4, wherein the locking member has a first configuration that restricts translational motion of the jaws away from one another and a second configuration that permits translational motion of the jaws away from one another, and wherein the locking member is spring-biased toward the first configuration.

Paragraph 6. The method of any of paragraphs 1 to 5, wherein the clamping instrument includes a frame member elongated parallel to the axis, wherein each of the jaws is connected to the frame member, and wherein one of the jaws is configured to be independently movable translationally and rotationally with respect to the frame member to adjust the distance between the jaws.

Paragraph 7. The method of any of paragraphs 1 to 6, wherein the clamping instrument includes a frame member elongated parallel to the axis, wherein one of the jaws is connected to the frame member via a threaded coupling, and wherein rotation of the one jaw about the axis adjusts the distance between the jaws.

Paragraph 8. The method of any of paragraphs 1 to 7, wherein the distance between the jaws is adjustable through a larger range by the translational motion than the rotational motion.

Paragraph 9. The method of any of paragraphs 1 to 8, further comprising a guide member configured to be mated with the clamping instrument by motion parallel to the axis, wherein the step of creating a hole includes a step of guiding a boring tool along the axis using the guide member.

Paragraph 10. The method of any of paragraphs 1 to 9, further comprising a step of placing the female fastener at one end of the hole after the step of creating a hole and before the step of attaching.

Paragraph 11. The method of paragraph 10, wherein the step of placing the female fastener includes a step of moving the female fastener along the axis into the clamping instrument.

Paragraph 12. The method of paragraph 11, further comprising a step of assembling the female fastener with an insertion tool therefor, wherein the step of moving the female fastener along the axis includes a step of mating the insertion tool with the clamping instrument along the axis.

Paragraph 13. The method of paragraph 12, further comprising a step of locking the insertion tool after the insertion tool has been mated with the clamping instrument, to prevent rotation of the insertion tool and the female fastener about the axis.

Paragraph 14. A method of fixing bone, the method comprising, in any order: (A) compressing a bone with a clamping instrument, such that the clamping instrument is attached to the bone; (B) creating a hole through the bone on an axis extending through the clamping instrument on opposite sides of the bone; (C) placing a male fastener into the hole; (D) mating an insertion tool with the clamping instrument after the step of creating a hole, wherein the insertion tool carries a female fastener; and (E) attaching a leading end of the male fastener to the female fastener.

Paragraph 15. The method of paragraph 14, further comprising a step of locking the insertion tool to the clamping instrument.

Paragraph 16. The method of paragraph 14 or 15, wherein the clamping instrument includes a pair of tubes arranged coaxially with one another, and wherein the step of mating includes a step of inserting at least a portion of the insertion tool into one of the tubes.

Paragraph 17. A system for bone fixation, comprising: a clamping instrument including a first tube and second tube arranged coaxially with one another, the first tube and the second tube being configured to collectively apply compression to bone and having a distance from one another that is adjustable independently by translational motion and rotational motion of the first tube and the second tube relative to one another. Paragraph 18. The system of paragraph 17, wherein the clamping instrument includes a locking member configured to selectively restrict translational motion of the tubes away from one another while permitting translational motion of the tubes toward one another.

Paragraph 19. The system of paragraph 18, wherein the locking member has a first configuration that selectively restricts translational motion of the tubes away from one another and a second configuration that permits translational motion of the tubes away from one another, and wherein the locking member is spring-biased toward the first configuration.

Paragraph 20. The system of any of paragraphs 17 to 19, wherein the clamping instrument includes a frame member elongated parallel to the axis, wherein each of the tubes is connected to the frame member, and wherein one of the tubes is configured to be independently movable translationally and rotationally with respect to the frame member to adjust the distance between the tubes.

Paragraph 21. The system of any of paragraphs 17 to 20, wherein the clamping instrument includes a frame member elongated parallel to the axis, wherein one of the tubes is connected to the frame member via a threaded connection, and wherein rotation of the one tube about the axis adjusts the distance between the tubes.

Paragraph 22. The system of any of paragraphs 17 to 21, wherein the distance between the tubes is adjustable through a larger range by the translational motion than the rotational motion.

Paragraph 23. The system of any of paragraphs 17 to 22, further comprising a guide member configured to be mated with one of the tubes of the clamping instrument by motion parallel to the axis, wherein the guide member is configured to guide a boring tool into the bone along the axis.

Paragraph 24. The system of any of paragraphs 17 to 23, further comprising a male fastener and a female fastener configured to attach to one another.

Paragraph 25. The system of paragraph 24, further comprising an insertion tool configured to be mated with the second tube while carrying the female fastener.

Paragraph 26. The system of paragraph 24 or 25, wherein the insertion tool is configured to be locked to the clamping instrument such that the female fastener is prevented from rotating while the male fastener is being attached to the female fastener.

Paragraph 27. A method of fixing a bone including a first bone fragment and a second bone fragment separated by a fracture, the method comprising, in any order: (A) attaching a clamping instrument to the first bone fragment and the second bone fragment by contacting an exterior portion of both fragments; (B) reducing the fracture by manipulating the bone fragments towards an anatomic shape using the clamping instrument; (C) forming a hole through the bone fragments such that a gliding hole is made for a first fastener; (D) measuring hole depth for first fastener length; (E) inserting a first fastener and engaging a second fastener, the second fastener being entirely exterior to the bone fragments, held by the clamping instrument, and incorporating a locking mechanism; and (F) compressing the fracture with the fasteners.

Paragraph 28. The method of paragraph 27, wherein a location of a skin incision is marked by an accessory attached to the clamping instrument.

Paragraph 29. The method of paragraph 27 or 28, comprising reducing the fracture by sliding a portion of the clamping instrument inwardly along a bar.

Paragraph 30. The method of any of paragraphs 27 to 29, further comprising reducing the fracture by rotating a portion of the clamping instrument about the axis of the intended hole.

Paragraph 31. The method of any of paragraphs 27 to 30, wherein a detachable guide is used to guide a boring tool through the bone fragments.

Paragraph 32. The method of any of paragraphs 27 to 31, wherein a detachable guide is used to aid the measuring of the hole depth.

Paragraph 33. The method of any of paragraphs 27 to 32, wherein a component attachable/detachable from the clamping instrument is used to retain the second fastener.

Paragraph 34. The method of any paragraph 27 to 33, wherein the second fastener's locking mechanism includes of a non-metallic material that is integrated into or forms the entire fastener.

Paragraph 35. The method of any of paragraphs 27 to 34, wherein the fasteners engage one another either via preformed internal threads of the second fastener or threads being formed in the second fastener by the first fastener.

Paragraph 36. The method of any of paragraphs 27 to 35, wherein the second fastener is secured in the clamping instrument and prevented from rotating about the axis of the hole by a geometrically-shaped pocket matched to a shape of the second fastener.

Paragraph 37. The method of any of paragraphs 27 to 36, further comprising a first washer about the major shaft diameter of the first fastener secured to the bone by the head of the first fastener and/or a second washer secured the bone by the shaft of the first fastener and the head of the second fastener. The washers may either be guided to bone through portions of the clamping instrument or placed on the bone prior to attaching the clamping instrument.

Paragraph 38. The method of any of paragraphs 27 to 37, wherein a plate is fastened to the bone by the fasteners.

Paragraph 39. The method of any of paragraphs 27 to 38, wherein the method of placing the fasteners is repeated in order to place a plurality of fasteners.

Paragraph 40. The method of any of paragraphs 27 to 39, further comprising selecting the first fastener from a set of fasteners having a plurality of different lengths such that a shaft of the selected first fastener operatively engages the second fastener.

Paragraph 41. The method of any of paragraphs 27 to 40, further comprising a step of selecting the first fastener shaft major diameter and accompanying second fastener inner diameter based on bone size.

Paragraph 42. The method of any of paragraphs 27 to 41, wherein the fracture fixation takes place in osteoporotic bone.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

I claim:

1. A system for fixing bone, comprising:
   a clamping instrument including a first tube and a second tube, the tubes having an adjustable separation from one another while remaining coaxially aligned with one another on an axis and being configured to apply pressure to opposite skies of a bone to compress the bone;
   a first fastener configured to pass through the first tube on the axis; and
   a second fastener configured to attach to the first fastener and to pass through the second tube on the axis; and
   an insertion tool that mates with the second fastener, the insertion tool being configured to be inserted into the second tube along the axis while the second tube remains engaged with bone;
   wherein the insertion tool is configured to be locked to the clamping instrument.

2. The system of claim 1, where the separation between the first tube and the second tube is adjustable by translational motion of the tubes relative to one another and also by rotational motion of the tubes relative to one another.

3. The system of claim 1, wherein the clamping instrument includes a frame that holds each of the tubes, and wherein at least one of the tubes is in threaded engagement with the frame that permits rotation of the at least one tube about the axis.

4. The system of claim 1, wherein the insertion tool defines an axial channel that extends through the insertion tool.

5. The system of claim 4, further comprising a drill bit having an outer diameter that matches a diameter of the axial channel.

6. The system of claim 1, wherein the insertion tool has a graspable handle configured to remain outside the second tube when the insertion tool is locked to the clamping instrument.

7. The system of claim 1, further comprising a drill bit having an outer diameter that substantially matches an inside diameter of the tube.

8. The system of claim 1, wherein the first fastener has an external thread, wherein the second fastener has a barrel, a flange, and a head, and wherein the external thread of the first fastener is configured to be engaged with an interior surface of the barrel to produce threaded engagement that attaches the fasteners to one another.

9. A system for fixing bone, comprising:
a clamping instrument including a first tube and a second tube, the tubes having an adjustable separation from one another while remaining coaxially aligned with one another on an axis and being configured to apply pressure to opposite sides of a bone to compress the bone parallel to the axis;
a first fastener configured to pass through the first tube on the axis;
a second fastener configured to pass through the second tube on the axis; and
an insertion tool configured to carry the second fastener into the second tube along the axis, and to hold the second fastener and prevent it from turning while the first fastener is being turned to attach the fasteners to one another.

10. A method of fixing bone, the method comprising, in any order:
compressing a bone with a clamping instrument, wherein the clamping instrument has a first tube and a second tube that apply pressure to opposite sides of the bone and are coaxially aligned with one another on an axis;
creating a hole through the bone on the axis;
passing a leading end of a first fastener through the first tube and into the hole;
inserting a second fastener into the second tube along the axis; and
attaching the first and second fasteners to one another;
wherein the steps of creating, passing, inserting, and attaching are performed while the first and second tubes remain engaged with the bone.

11. The method of claim 10, further comprising a step of mating the second fastener and an insertion tool with one another, wherein the step of inserting includes a step of manipulating the insertion tool while the insertion tool carries the second fastener.

12. The method of claim 11, wherein the step of inserting includes a step of locking the insertion tool to the clamping instrument.

13. The method of claim 11, wherein the insertion tool defines an axial channel, and wherein the step of creating a hole includes a step of guiding a drill bit into the bone using the axial channel.

14. The method of claim 13, wherein the hole includes a bore and a counterbore, wherein the second tube defines a channel, and wherein the step of creating a hole includes a step of forming the counterbore with a drill bit guided into the bone using the channel of the second tube.

15. The method of claim 10, wherein the step of creating a hole includes a step of advancing a tip of a drill through the second tube and into contact with the bone.

16. The method of claim 10, wherein the step of creating a hole includes a step of forming a bore through the bone, and a step of forming a counterbore extending into the bone near the second tube.

17. The method of claim 16, wherein the step of attaching includes a step of engaging a surface of the bone with a flange of the second fastener, such that a barrel of the second fastener is located inside the counterbore formed in the bone.

18. The method of claim 10, further comprising a step of placing a gauge into the hole to measure a dimension corresponding a length of the hole, and a step of selecting a first fastener from a set of first fasteners of different length based on the dimension measured.

* * * * *